United States Patent
Redko et al.

(10) Patent No.: US 7,355,395 B2
(45) Date of Patent: Apr. 8, 2008

(54) METHOD AND APPARATUS FOR EDDY CURRENT-BASED QUALITY INSPECTION OF DRY ELECTRODE STRUCTURE

(75) Inventors: Volodymyr Redko, Coral Springs, FL (US); Volodymyr Khandetskyy, Dnipropetrovsk (UA); Peter Novak, Ft. Lauderdale, FL (US); Elena Shembel, Coral Springs, FL (US); Satoshi Kohara, Kanagawa (JP)

(73) Assignee: Enerize Corporation, Coral Springs, FL (US)

( * ) Notice: Subject to any disclaimer, the term of this patent is extended or adjusted under 35 U.S.C. 154(b) by 0 days.

(21) Appl. No.: 11/245,398

(22) Filed: Oct. 6, 2005

(65) Prior Publication Data

US 2006/0109003 A1    May 25, 2006

Related U.S. Application Data

(60) Provisional application No. 60/616,440, filed on Oct. 6, 2004.

(51) Int. Cl.
*G01N 27/82* (2006.01)
*B07C 5/344* (2006.01)

(52) U.S. Cl. .................. 324/240; 209/574; 324/238

(58) Field of Classification Search ............. 324/240, 324/237, 238; 209/574
See application file for complete search history.

(56) References Cited

U.S. PATENT DOCUMENTS

| | | | |
|---|---|---|---|
| 6,958,603 B2 | 10/2005 | Kondo | 324/239 |
| 2002/0027095 A1* | 3/2002 | Tanii et al. | 209/214 |
| 2004/0095136 A1 | 5/2004 | Artinger et al. | 324/228 |

* cited by examiner

*Primary Examiner*—Reena Aurora
*Assistant Examiner*—David M. Schindler
(74) *Attorney, Agent, or Firm*—Christopher & Weisberg, P.A.

(57) ABSTRACT

A system for non-destructive non-contact quality inspection of dry electrode units of energy storage includes an eddy current-based inspection system having a conveyor belt, and a hollow dielectric shell. An outer surface of the shell has a plurality of spaced apart measuring transducers. Each of the transducers include a feed-through eddy current probe and at least two strap capacitors spatially linked therewith. In the related method, an electrode unit to be inspected is placed on the conveyor belt and enters and moves through the dielectric shell. The electrode unit is excited using a magnetic field from the eddy current probe as it passes by each of the plurality of transducers, where eddy currents at a plurality of frequencies are induced in the electrode unit. The modulation characteristics of impedance at a plurality of frequencies are measured by the probes, and from the impedance data it is determined whether the electrode unit is defective.

13 Claims, 8 Drawing Sheets

METHOD AND APPARATUS FOR EDDY CURRENT-BASED QUALITY INSPECTION OF DRY ELECTRODE STRUCTURE

CROSS-REFERENCE TO RELATED APPLICATIONS

This application incorporates by reference in its entirety and claims priority to Provisional Application No. 60/616,440 entitled "METHOD AND APPARATUS FOR NON-DESTRUCTIVE NONCONTACT QUALITY INSPECTION OF DRY ELECTRODE STRUCTURE OF ENERGY STORAGE" which was filed on Oct. 6, 2004.

BACKGROUND OF THE INVENTION

1. Field of Invention

The invention relates to methods and apparatus for electromagnetic-based quality inspection of energy storage, for example batteries, supercapacitors, and fuel cells.

2. Description of the Related Art

The operating ability of chemical power sources is substantially determined by the quality of its structural components including cathode, separator, and anode. Inspection to monitor the quality of these structures allows removal of defective units which prevents use of faulty electrode units in the downstream technological component assembly operations, thus reducing system defects due to defective battery units.

Known in the art is a method of assessing quality of these structures by stabilizing the technological processes of preparing the initial products, applying them on a foil, and drying. Experience proves that even when the physico-chemical characteristics of the initial raw material components vary within a tolerable range, overall discrepancies may lead to the appearance of rejects. Therefore stabilization of the operating conditions when producing the structural components, and of their physico-chemical characteristics alone cannot provide adequate quality control for dry electrode units.

Any outer visual inspection is also not possible as the unit components are inaccessible. Opening of the coiled electrode structures for visual inspection is not viable since the active mass of electrodes for example the carbon, lithium-treated cobalt oxide, etc., deposited onto a current collector for example copper or aluminum electrode strip features high brittleness, and fractures during repeated deformations. Therefore, there is a need for anode and cathode strip integrity testing and inspection including continuity for coiled electrode units using noncontact and nondestructive testing methods.

SUMMARY OF THE INVENTION

In accordance with the invention an eddy current method is used for inspecting the quality of dry electrode units of energy storage, for example batteries, supercapacitors, and fuel cells. A system for non-destructive non-contact quality inspection of electrode units includes an eddy current-based inspection system having a conveyor belt, and a hollow dielectric shell. An outer surface of the shell has a plurality of spaced apart measuring transducers disposed thereon. Each of the transducers includes a feed-through eddy current probe and at least two strap capacitors spatially linked therewith. Thus, each of the transducers includes an eddy-current transducer (provided by the eddy-current probe) and a capacitance-based transducer (provide by the strap capacitors). In the related method, an electrode unit to be inspected is placed on the conveyor belt and enters and moves through the dielectric shell. The electrode unit is excited using a magnetic field from the eddy current probe as it passes by each of the plurality of transducers, where eddy currents preferably at a plurality of frequencies are induced in the electrode unit. The modulation characteristics of impedance (reactive resistance) at a plurality of frequencies are measured by the probes, and from the impedance data it is determined whether the electrode unit is defective.

A generatrix of the shell is preferably substantially parallel to a direction of movement of the conveyor belt, and a perpendicular section of the shell is similar in shape to a cross-sectional shape of the electrode unit. The method can further comprise the steps of registering an initial and final position of the electrode unit in a magnetic field emanated from each of said eddy current probes using the strap capacitors linked therewith, and correcting error in the introduced impedance of each of the eddy current probes that appears as a result of shifting of movement of the conveyor belt with the electrode unit in a direction that is perpendicular to a direction of the movement using signals obtained from the strap capacitors to provide corrected modulation characteristics of impedance.

The strap capacitors for each of transducers are preferably arranged on both sides of said eddy current probe at a substantially equal distance therefrom, and the plates of the strap capacitors are disposed on opposite sides of a surface of the shell opposite one another. in a preferred embodiment, each of the eddy current probes operates at plurality of different frequency. In this embodiment, the first eddy current probe to measure the electrode unit operates at a lowest of the plurality of different frequencies, wherein the plurality of eddy current probes other than the first eddy current probe are in comparison higher frequency probes.

A system for non-destructive non-contact quality inspection of dry electrode units of energy storage comprises an eddy current-based inspection system comprising a conveyor belt, and a hollow dielectric shell, an outer surface of said shell having a plurality of measuring transducers disposed thereon, each of said transducers including a feed-through eddy current probe and at least two strap capacitors spatially linked therewith. A generatrix of the shell is preferably substantially parallel to a direction of movement of the conveyor belt, and a perpendicular section of said shell is similar in shape to a cross-sectional shape of the electrode unit. The strap capacitors for each of transducer are preferably arranged on both sides of the eddy current probe at a substantially equal distance therefrom, and the plates of the strap capacitors are disposed on opposite sides of a surface of the shell opposite to one another. in one embodiment, a measuring transducer of a first of the eddy current probes to measure the electrode unit provides at least 5 times higher number of turns as compared to measuring transducers of other of the eddy current probes. The width of the conveyor belt preferably does not exceed a width of the electrode unit. The conveyor belt can be formed from a dielectric material with a dielectric loss tangent not exceeding $3 \times 10^{-3}$ within the metric wave band. The dielectric shell can be formed from a dielectric material which provides a loss tangent not exceeding $10^{-3}$ within the metric wave band, with a wall thickness of said shell not exceeding 5 mm.

BRIEF DESCRIPTION OF THE DRAWINGS

There is shown in the drawings embodiments which are presently preferred, it being understood, however, that the invention can be embodied in other forms without departing from the spirit or essential attributes thereof.

FIG. 1(a) is an exemplary simplified layout for a device for nondestructive noncontact inspection of the quality of dry electrode units, according to an embodiment of the invention showing strap capacitor plates and dielectric interlayers (in plane-parallel approximation), while

DETAILED DESCRIPTION OF THE INVENTION

Figure 1A:
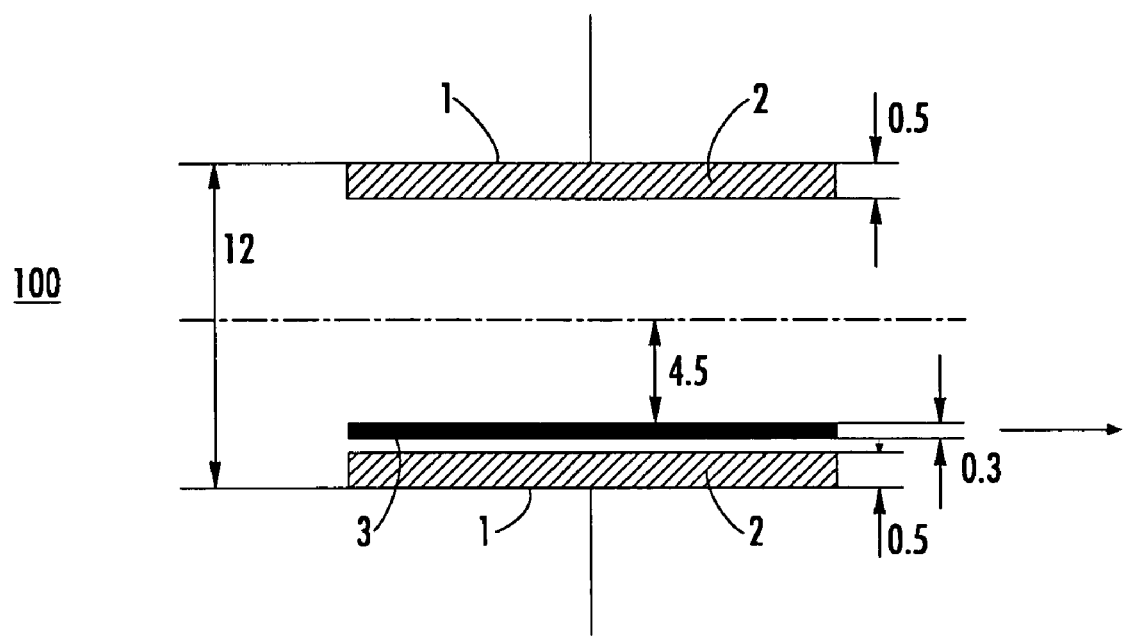
FIG. 1(b) shows a dry electrode unit on the conveyor belt between the capacitor plates.

Dry electrode units (jelly rolls) are comprised of coiled metallic strips of cathode and anode with double-sided coats, a separator strip therebetween and an outer shell made of a metal foil. The units include three (3) strips:

copper foil with a carbon layer applied to both sides thereof;

a separator made of a polypropylene porous strip (SELGARD™);

aluminum foil with a layer of lithium-alloyed cobalt oxide ($LiCoO_2$) mixed with carbon and a binder, applied to both sides thereof.

The metallic strips function as current inlets. The porous separator is subsequently impregnated with a liquid electrolyte.

As noted in the background, quality evaluation of dry electrode units comprised of metallic anode and cathode strips coated with an electrochemically active compound, and of the separator strip located therebetween, cannot be performed visually because after their assembly into a coil a reverse operation gives rise to cracking of the coat layers. The presence of cracks, chipping-off, coat spalling, as well as of short circuits in metallic layers leads to rejects, and introduces rejects into the downstream operations of power source manufacturing. For the purpose of timely detection of such defects, the invention provides systems and methods which place the electrode units on a conveyor belt that moves at a substantially constant speed through the inner space of a thin-walled cylindrically shaped dielectric shell containing a plurality of spaced apart primary measuring transducers arranged along its generatrix. The invention is adapted for automation and high volume inspection.

Each of the measurement transducers includes a pass-through eddy-current probe and a pair of strap-type capacitors spatially connected thereto. The term "strap" simply refers to plates or similar geometries disposed on the dielectric shell. As the electrode units move in sequence through the control zones of the primary transducers eddy currents where different frequencies are preferably used for excitation, the modulation characteristics of the introduced impedance of the eddy current probes are measured at these frequencies. The strap capacitors linked with the eddy current probe are used to detect the initial and the final position of the electrode unit in the magnetic field of each probe, and to correct the error of each probe that occurs due to the shift of the conveyor belt moving with the unit, perpendicular to the movement direction.

The different measurement frequencies preferably comprise the first probe encountered by the electrode unit using the lowest frequency, and the measurement frequency increasing with subsequent probes moving away from the first probe. The introduced reactive resistance of the first, relatively low frequency eddy current probe is preferably used for adjusting the sensitivity of the introduced active resistance of the second and subsequent eddy current probes operating in the high frequency range that varies with the change of the distance between the layers in the electrode units. The relation is determined of the adjusted amplitude value of the modulation characteristic of each high frequency eddy current probe for the faulty unit being tested to the average value obtained for all faultless units preceding the given faulty unit. The obtained relations are preferably compared for each operating frequency of the high frequency range, while determining the maximum relation that provide information to identify a level of defectiveness of the coats of the cathode and anode metallic strips of the given dry electrode unit.

FIG. 1(a) shows an exemplary layout diagram in plane-parallel approximation for a device for nondestructive non-contact inspection of the quality of dry electrode units 100, according to an embodiment of the invention. Dimensions (in mms) shown in FIGS. 1(a) (and 1(b) and other figures) are for reference only, and in no way limit the invention. Device 100 includes capacitor plates 1 and a thin walled dielectric shell 2 inside of plates 1, and a conveyor belt 3.

The electrode units to be inspected (not shown) are placed on the conveyor belt 3 that preferably moves at a substantially constant speed inside shell 2 whose generatrix is parallel to the movement direction of the conveyor belt 3 The shell 2 is preferably cylindrically shaped. The section shape of the shell in the plane that is perpendicular to its generatrix is preferably similar to the shape of the electrode unit cross-section, such as elliptical, or cylindrical (not shown). The width of the conveyor belt 3 preferably does not exceed the width of the electrode unit, while the strip surface is parallel to the symmetry plane of shell 2 and is shifted relative to the shell to a distance preferably approximately equal to the half of the electrode unit thickness. Thus, the electrode unit to be inspected moving on the conveyor belt 3 is placed within the inner space of the cylindrical shell 2 symmetric relative to the symmetry plane of the shell 2.

Figure 2:
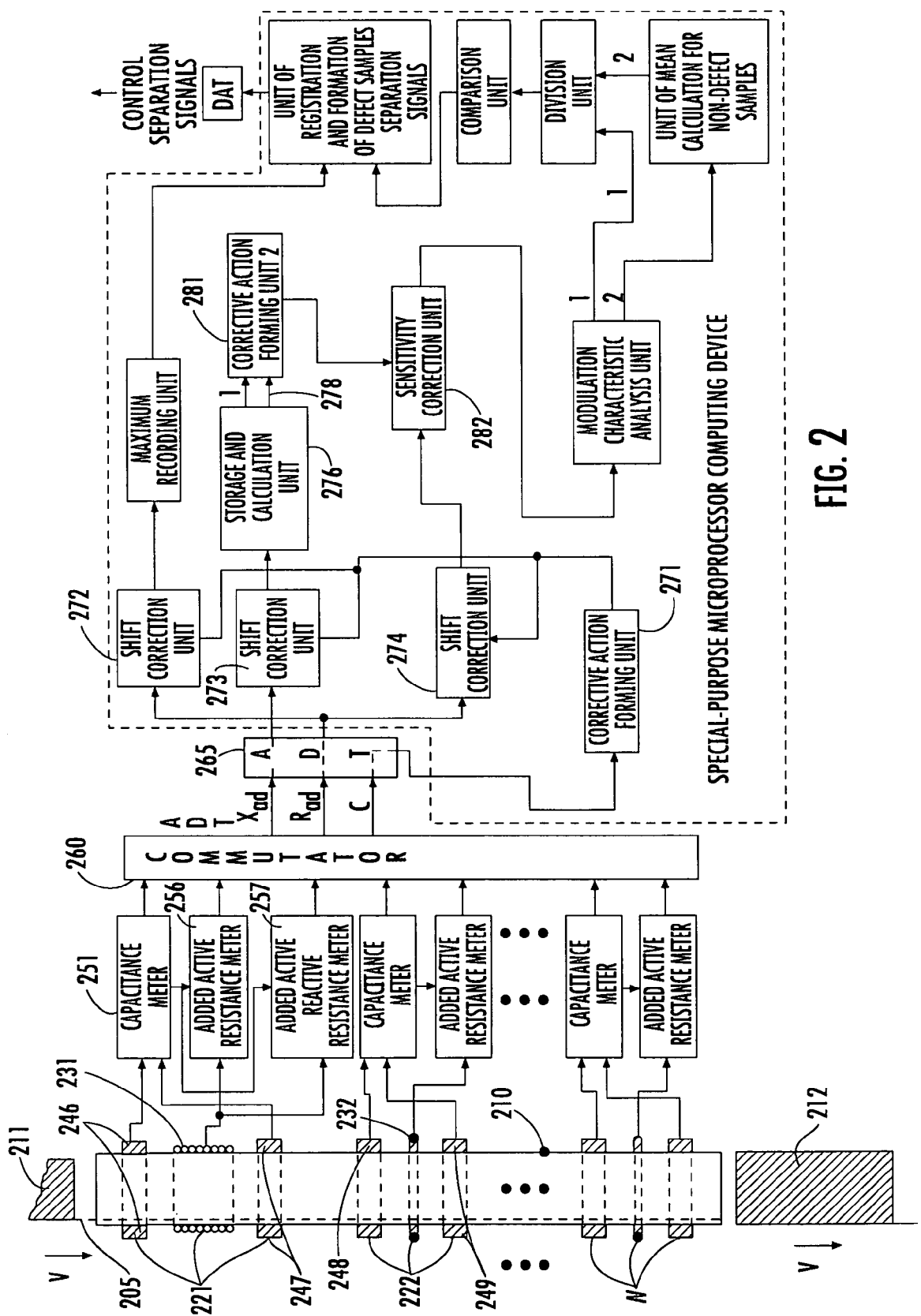
FIG. 2 is a block diagram of a device for nondestructive noncontact quality inspection of dry electrode units.

On the outer surface of the dielectric shell 2 along its generatrix, a plurality of integrated primary measuring transducers are arranged, each containing a feed-through eddy current probe and two strap capacitors spatially linked therewith. Each of the transducer functions as feed-through eddy current probes spatially linked with two strap capacitors arranged at both sides of the eddy current probe at preferably an equal distance therefrom. The eddy current probe of the first measuring transducer (seen by the electrode units) is a multiple-turn device while the subsequent ones have fewer turns, such as 3, 2 or 1 (single turn). Such an embodiment is shown in FIG. 2.

Figure 1B:
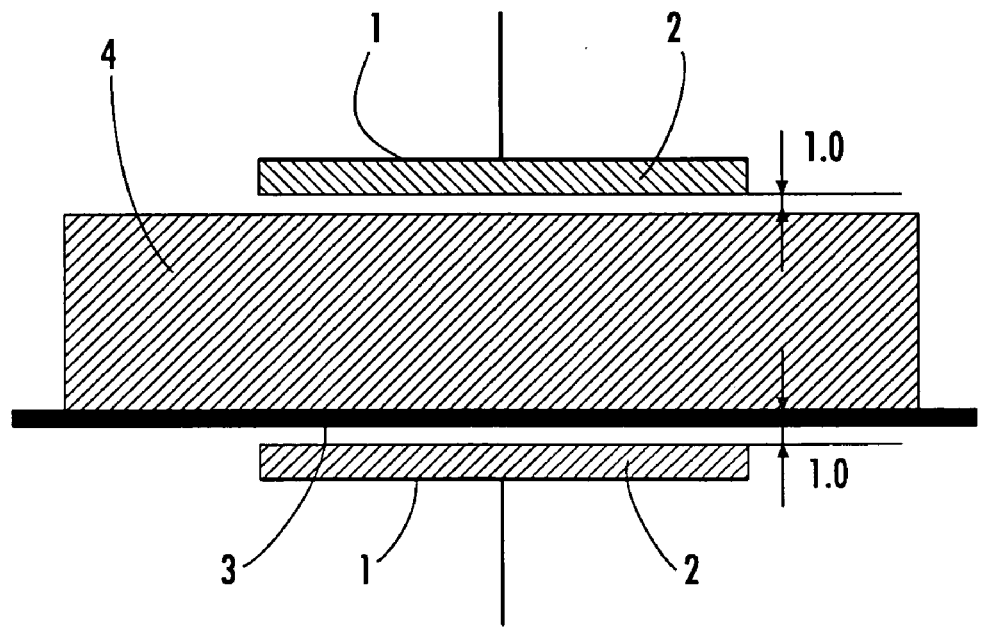

FIG. 1(b) shows a dry electrode unit 4 on the conveyor belt 3 between the capacitor plates 1 of dielectric shell 2. As the electrode unit 4 passes in succession through the inspection zones of the primary measuring transducers, eddy currents of various frequencies are excited and at these frequencies the modulation characteristics of the introduced impedance of the eddy current probes are measured.

Registration of the initial and final position of the electrode unit in the magnetic field of each eddy current probe is performed using the strap capacitors linked to the eddy current probe. The capacitors are also preferably used in correcting the error of the introduced impedance of each eddy current probe that appears as a result of the shift of the moving conveyor belt 3 with the unit in the direction that is perpendicular (lateral; on the plane of the belt) to the movement direction of the belt.

The correction of the sensitivity to the introduced active resistance of the second and subsequent eddy current probes operating in the high frequency band that changes with the change of the distance between the layers in the electrode units is performed using the introduced reactive resistance of the first, relatively low frequency eddy current probe.

Identification of the electrode units having defects in the coats of the metallic cathode and anode strips is preferably performed according to the adjusted values of the introduced active resistance of the high frequency probes when they exceed a predetermined threshold value selected. In such case, current averaging is performed of the adjusted values of the introduced active resistance of each high frequency eddy current probe for faultless units preceding the given faulty electrode unit, determining the relation of the adjusted amplitude value of the modulation characteristic of the introduced active resistance of each high frequency eddy current probe for the faulty unit being controlled to the average value of the introduced active resistance of the same probe obtained for all faultless units preceding the given faulty unit. The obtained relations can be compared for each operating frequency of the high frequency band, while determining the maximum relation that characterizes the defectiveness degree of the coats on the metallic cathode and anode strips of the given dry electrode unit.

The strap capacitors of each primary measuring transducer are preferably arranged on both sides of the eddy current probe at an equal distance therefrom while the plates of each of the capacitors 1 are found on the opposite sides of the surface of shell 2 opposite to each other. The initial position of the electrode unit 4 in the magnetic field of each eddy current probe is preferably registered at the moment when the capacitances of its capacitors pass through the positive value gradients and reach approximately identical values.

The electrode units with closed metallic layers are detected according to the value of the introduced active resistance of the first eddy current probe operating at a substantially lower frequency.

After registering the initial position of the electrode unit the plates of the capacitors are switched in such a way that the plates of the newly formed first capacitor are found on the one side of the electrode unit while the plates of the second capacitor are on the other side. From the newly formed capacitors that one is selected as the operating capacitor whose capacitance increases when the electrode unit is moved in the control zone of the given primary measuring transducer.

The final position of the electrode unit in the magnetic field of each eddy current probe is registered at the moment when the capacitance of the corresponding operating capacitor passes the negative gradient of the value. The modulation characteristic of the introduced impedance of the eddy current probe is measured within the interval between the initial and the final positions of the electrode unit.

The capacitance value of the operating capacitor is used for determining the unit shift value in the direction perpendicular to the conveyor belt movement direction, and this value is used in setting the value of the correcting coefficient that takes into consideration the distribution of the magnetic field intensity in the radial plane of the feed-through eddy current probe. The inverse switching of the plates in the capacitors of the given primary transducer for restoring the initial position is performed within the time interval between the final position of the given unit in the control zone of the previous primary measuring transducer and the initial position in the control zone of the subsequent primary transducer.

Current averaging is preferably performed of the corrected values of the introduced reactive resistance of the first relatively low frequency eddy current probe for all controlled samples that precede the given sample. The corrected value of the introduced reactive resistance of the first eddy current probe for the given unit is stored and then used for correcting the sensitivity of the second and subsequent eddy current probes when they will successively control this electrode unit. The sensitivity of the introduced active resistance of the second and subsequent eddy current probes will be corrected by multiplying the introduced active resistance of each probe by the relation of the averaged value of the introduced reactive resistance of the first probe for all the electrode units preceding the given unit to the value of the introduced reactive resistance of the first probe for the given unit.

The minimum distance between the edge turn of the eddy current probe and the nearest end face of the strap capacitor plate is selected taking into regard the typical for the whole batch shape and geometrical dimensions of the electrode unit samples, as well as of the electrode unite inner space factor (the space containing cathode and anode strips). The width of the capacitor plates 1 generally do not exceed 5 mm, while in the body of each plate at an identical interval along the plate at the side of the eddy current probe narrow slots are preferably cut through the whole thickness whose length equals 80% of the plate width. Both plates of each strap capacitor in their initial condition have identical geometrical dimensions, are located on the shell opposite each other, the gaps between the ends of the plates on both sides are equal and in their size do not exceed 10% of the length of each plate. The thickness of the capacitor plates generally does not exceed 0.1 mm while the turns of the eddy current probe and the plates of the capacitors are placed in the shell body recesses so that the thickness of the shell material immediately under the turns of the probe and the capacitor plates is within 0.5–1 mm.

The surface of the capacitor plates should have minimal roughness and increased electrical conductivity. The electric field of the capacitors is of harmonic character, the field frequency of all the capacitors being equal.

The minimum distance between the continuous lateral end face of the plates in the second strap capacitor of the previous measuring transducer and the opposite lateral end face of the plates of the first strap capacitor of the subsequent measuring transducer is of the value that 1.5 times exceeds the maximum distance between the oppositely arranged plates of the capacitor.

The eddy current probes of the second and subsequent measuring transducers contain from one to three turns of wire of not less than 1 mm diameter, while the eddy current probe of the first measuring transducer contains at least a 5 times higher number of turns.

The width of the conveyor belt preferably does not exceed the width of the electrode unit, with the strip surface being parallel to the symmetry plane of the shell and shifted relative to it to a distance equal to the half of the electrode unit thickness.

The conveyor belt is preferably made of a dielectric material with a dielectric loss tangent not exceeding $3 \times 10^{-3}$ within the metric wave band. The material of the dielectric shell should have a dielectric loss tangent not exceeding $10^{-3}$ within the metric wave band, with the shell wall thickness not exceeding 5 mm.

A block diagram for a system for nondestructive noncontact quality inspection of dry electrode units of energy storage is shown in FIG. 2 which schematically shows a thin cylindrically shaped shell 210 surrounding a conveyor belt 205 moving at a substantially constant speed V. On the belt 205, a first and second electrode unit, 211 and 212, are disposed. On the surface of the shell 210 along its generatrix the primary measuring transducers are arranged that are designated 221, 222 and N. Each primary measuring transducer includes a feed-through eddy current probe 231 and 232, respectively, and strap type capacitors 246 and 247, and 248 and 249 arranged at both sides thereof at preferably an identical distance therefrom, the eddy current probes 221 and 222, respectively. The distance between eddy-current probes 221 and 222 and each strap capacitor is preferably equal to about 1.8 (such as 1.5 to 2.1) times the length of the eddy current probe. Preferably, the first eddy current probe has more turn than successive eddy current probes. Eddy current probe 221 is shown in FIG. 2 having 5 turns while eddy current probe 222 is shown having a single turn.

Connected to the plates of the strap capacitors are the capacitance measuring circuits 251 that also contain structure for commutating 260 the plates of the capacitors and for determining the capacitance sign change. Commutating refers to signal from capacitor moving via electronic circuit and correcting the signal from eddy-current probe. Connected to the eddy current probes are the circuits for measuring the introduced active resistance 256, while to the first eddy current probe is also connected a circuit for measuring the introduced inductance 257.

The circuits for measuring the introduced active resistance of the probes 256 are similar, each containing a high frequency generator of sinusoidal or other AC voltage signal, a buffer stage of the current amplifier, a resonant circuit with an eddy current probe connected to the buffer stage outlet through a coupling element. The voltage is preferably taken from the resonant circuit through a matching current amplifier, fed to the amplitude detector and further passed to the signal analog processing circuit that carries out the signal level compensation of the unloaded probe and its stabilization. The value of the introduced reactive resistance 257 is generally measured using a frequency detector.

The outlets of all the capacitance meters 251, of the introduced active resistance meters 256, as well as of the introduced reactive resistance meter 257 are preferably connected to the inlets of the controlled commutator. To the outlet of the commutator 260 is a three-inlet analog-to-digital converter 265. To the inlet of the latter at the given time interval come the signals of the meters of that primary transducer in whose control zone is registered the electrode unit being inspected. When the given electrode unit 211 or 212 passes to the control zone of the next primary transducer that is registered by the respective gradients of the capacitances of its capacitors, the inlet of the analog-to-digital converter will be switched via the controlled commutator to the outlets of the meters of this new primary transducer.

The outlets of the analog-to-digital converter are preferably connected to the inlets of the specialized microprocessor calculator. The calculator units shown on its block diagram can be realized in the software, hardware, as well as in an integrated variant.

The capacitance values of the capacitors can be converted to a digital code are fed into corrective action forming unit 271 where the shift value d is determined and the value of the coefficient $\gamma$ is formed. The output signal of this unit enters the respective inlets of the shift correction units 272, 273 and 274, where multiplying of the corresponding values of the introduced active resistance $R_{ad}$ and of the introduced reactive resistance $X_{ad}$ by the value $\gamma$ is performed. In the diagram the three shift correction units are specified separately: for $R_{ad}$ of the high frequency probes, for $R_{ad}$ of the low frequency probe, and for $X_{ad}$ of the low frequency probe. This is connected with the different band of the input digital signals for each of these parameters.

The maximum specifying unit determines the amplitude of the modulation characteristic of the introduced active resistance of the first eddy current probe characterizing the contact availability and value in the closed metallic layers of the electrode unit 211 or 212. This value is registered, a corresponding signal is formed and separation of such faulty units is carried out.

The storing and calculation unit 276 performs the current averaging of the corrected values of the introduced reactive resistance of the first eddy current probe for all the inspected units preceding the given one. This signal comes to the outlet 1 of the unit. Besides, stored in this block is the corrected value of the introduced reactive resistance of the first eddy current probe for the given unit being controlled within the current time interval with the help of the combined primary transducers. This signal comes to the outlet 278 of the unit.

corrective action forming unit 281 is for forming the correcting influence performs the calculation of the relation of the signals entering its first and second inlets. In the sensitivity correction unit 282 the value of the introduced active resistance of the given high frequency eddy current probe coming from the corresponding shift correction unit is multiplied by the relation calculated in the unit 281 for forming the correcting action.

Next is analyzed the modulating characteristic of the corrected introduced active resistance of the high frequency probe. The faulty and faultless (non-defect) units are separated by comparing with the threshold specified for each probe. The value $R_{ad}^{(nd)}/\omega L_0$ is the own inductive resistance of the probe, nd—non-defect) for the faultless (non-defect) electrode unit enters the outlet 2 and further the current averaging unit $R_{ad}^{(nd)}/\omega L_0$ of the faultless (non-defect) units. Here separately for each eddy current probe of the high frequency band averaging is carried out of the relative introduced active resistances for all faultless units that had already passed the inspection.

If a faulty electrode unit is revealed in the unit of modulation characteristics analysis the respective value of $R_{ad}^{(nd)}/\omega L_0$ arrives at the outlet 1 of the analysis unit and further passes to the relation calculating unit where calculation of the relation $R_{ad}^{(nd)}/\omega L_0$ is performed for each high frequency eddy current probe to the average for the faultless units value $R_{ad}^{(nd)}/\omega L_0$ for the same probe. Such relations are formed for all the high frequency probes which registered the defectiveness of the unit.

In the comparing unit the obtained for each probe relations are compared and the maximum relation is determined that characterizes the defectiveness degree of the coats on the electrodes of the given unit. This relation is recorded. The respective signals for separating the defective units are formed, and their digital-to-analog conversion is performed. The units with coat defects are separated into several groups according to the maximum relation value determined during the comparison process and registered in the registration unit.

For detecting defects such as cracks and chipping-offs in the layers of low-conducting coats of the metallic cathode and anode strips it is necessary to obtain eddy current data from the volume of the metallic strips into the layers of the coat while providing the flow through these layers of high density eddy currents. It is generally necessary to substantially increase the frequency of the primary magnetic field inducing eddy currents in the sample. In such case, as was shown by experiments, the results being described herein relative to Example 1, that the high frequency eddy current probes of the second and subsequent measuring transducers should contain not more than 3 turns of wire, while the relatively low frequency eddy current probe of the first measuring transducer should preferably contain minimum 5 times higher number of turns. To provide high Q-factor eddy current probes, and correspondingly a high sensitivity to the coat defects, the wire diameter of the turns in the probes should generally be not less than 1 mm. In operation, the eddy current transducers are generally powered with currents of different frequencies.

Each strap capacitor preferably contains two plates of identical geometrical dimensions placed on the shell 2 opposite each other. The gaps between the ends of the plates on both sides are preferably essentially identical and in their size do not exceed about 10% of the length of each plate. Taking into regard the marginal thickness of the plates (0.1 mm) allows not taking into account the capacitance between the end faces of the plates. The width of each plate does not exceed 5 mm. An approximate calculation of the capacitance of such a capacitor for the shape and dimensions of the dielectric shell corresponding to a conventional jelly roll unit is demonstrated in Example 2. According to the calculation, the capacitance value of an unloaded capacitor (without a sample) equaled $C_e$=0.16 pF. The capacitance value of the capacitor when an electrode unit is found between its plates (a loaded capacitor) equaled $C_1$=0.91 pF.

Each primary measuring transducer contains two capacitors that are arranged at both sides of the eddy current probe. These capacitors are used for registering the initial and the final positions of the electrode unit in the magnetic field of the given eddy current probe, also, they take part in the correcting procedure.

The invention includes measures for reducing the influence of the plates of capacitors on the Q-factor of the eddy current probe. First, the operation at metric wave length band (meter range of wavelength) of the eddy current magnetic field results that the eddy currents in the capacitor plates are practically concentrated on the surface of the plates, therefore the active losses of energy of the probe primary field in the metal of the plates is minimal. These losses are further reduced due to the smooth surface of the plates (the minimum possible roughness level is not worse than 0.1 V (special for worse), and the presence of the surface layer of increased conductance due, for example, to coating of the copper plates with a thin layer of silver.

Second, the capacitor plates themselves are rather thin, as their thickness should generally not exceed 0.1 mm, besides, the turns of the eddy current probe and the capacitor plates are arranged in the same plane (the symmetry plane of the turns coincides with the symmetry plane of the plates). The normal to the turn plane component of the magnetic field intensity of the eddy current probe excites in the plate the currents that flow in the planes perpendicular to the plate surfaces. The resultant trajectories of the oppositely directed currents on the lower and upper surfaces of the plate are located (due to the low thickness of the plates) close to each other. Therefore these currents are to a substantial degree compensated by the interaction of their magnetic fields.

Third, in the body of a plate at an identical interval along its length on the side of the eddy current probe narrow slots are preferably cut through its whole thickness of a length that equals 80% of the plate width. As a result, the eddy current excited both by the normal and the tangential relative to the turn plane component of the magnetic field intensity meets on its way insurmountable obstacles, and as a result it breaks into small trajectories. In such case the interaction of the eddy current field with the primary field is weakened while the influence of the plate on the eddy current Q-factor gets reduced. The width of each slot is of the order of 50 µm, while the quantity of the slots is of the order of 10 per plate. In such case for a plate of 5×40 mm in dimension (as in Example 1) the relation of the total area of the slots to the total area of a plate is 1%, and this has practically no influence on the capacitance value of the capacitor.

The electric field of the strap capacitors has a harmonic character, while the field frequency of the capacitors in all primary measuring transducers is generally identical.

Of importance is selecting the distance $z_0$ between the turn of the eddy current probe and the nearest to it end face of the capacitor plate. In Example 3 for that purpose a calculation was made of the intensity components of the magnetic field of the current turn, here in FIG. 10 the distance $z_0$ is shown. The calculation results show that with a tolerable error the distance $z_0$ can be selected as $z_0=0.4R$. The above described methods of reducing the plate influence on the Q-factor of an eddy current probe allow a further reduction of this error.

The dry electrode units of storage battery power sources can be shapes other than cylindrical. When passing from cylindrically shaped electrode units of perpendicular section in the form of a circle to units of a section in the form of an ellipse, as an equivalent section diameter should be used the minimum distance between the opposite surfaces of the unit measured in the center of the section symmetry. Hence, when the opposite edges of the ellipse-like unit approach each other, its equivalent diameter, and, correspondingly, its radius get reduced thus allowing to reduce the absolute value $z_0$. A transition to controlling more lengthy units, on the contrary, permits to increase $z_0$, since a longer noncontrolled zone can be allowed at the edge of the sample.

As noted above, the electrode unit has a laminar structure and consists of coiled metallic strips of cathode and anode with coats applied thereto on both sides, including the polypropylene separator strip arranged between the cathode and anode. The lines of force of the magnetic field of the feed-through eddy current probe inside of the unit are found along its generatrix and are coincident with the planes of the unit layers. In such case a fraction of the field inside of the unit is found within the volume of the cathode and anode metallic strips while having a rather small depth of penetration about 9 to 100 μm. A fraction of the field found between the metallic strips has the spatial characteristics that are comparable with the characteristics within the free space. The degree of the field intensity "loss" within the electrode unit volume depends on the relation of the total thickness of the metallic electrode strips to the equivalent unit diameter, that is on the space factor $\chi$ of the inner electrode unit space containing the cathode and anode strips. And since the value $z_0$ (see FIG. 10) was calculated by the Inventors according to the characteristics of the field in the free space, therefore, taking into regard the space factor $\chi$ it can be reduced, in the first approximation, proportionally to the value $\chi$. The width of the plates of the capacitors arranged at both sides of the eddy current probe limited by us on the top by the value of 5 mm can be reduced while increasing the sensitivity and accuracy of the capacitance measuring units.

The initial position of the electrode unit in the magnetic field of the eddy current probe of each primary transducer is preferably registered at the moment when the capacitances of both capacitors arranged at both sides of the eddy current probe pass through the positive gradients of the values (in accordance with the calculation performed in Example 2 they increase from $C_e=0.16$ pF to $C_1=0.91$ pF) and obtain approximately equal values $C_1^{\;1}=C_1^{\;2}$. As follows from TABLE 2 of Example 2, these values practically do not change with the shift of the electrode unit in the direction perpendicular to the capacitor plates due to the shift of the conveyor belt in the process of movement.

After registering the initial position of the electrode unit the plates of the capacitors of the primary measuring transducer are changed-over. In this case the plates of the newly formed first capacitor are arranged at one side of the controlled electrode unit (one on the left and the other on the right of the eddy current probe) while the plates of the second capacitor are arranged at the other side of the electrode unit in the same manner.

When the conveyor belt with the electrode unit is shifted in the direction perpendicular to its movement (that is either down or up) the capacitance of one of the capacitors gets increased while that of the second one gets decreased depending on the direction of the unit shift. The capacitor whose capacitance is increasing is selected as the operation capacitor in such case.

The capacitance of the operating capacitor $C_w$ consists of the capacitances of the two capacitors $C_a$ connected in series, or of the two capacitors $C_b$ connected in series (see Example 2). The capacitors are connected on the metallic foil of the unit shell. Let, for example select as the operating the first capacitor comprised of capacitors $C_a$. Then $C_w=C_a/2$. As follows from TABLE 2 of Example 2, when the unit is symmetrically arranged on the conveyor belt (shift d=0) $C_a=1.63$ pF, hence $C_w=0.815$ pF.

When the electrode unit in the process of the conveyor belt movement leaves the electric field zone of one plate of the operating capacitor, then the corresponding capacitance between this plate and the metallic surface of the shell gets abruptly and substantially reduced, leading to a corresponding and substantial reduction of the total capacitance of the operating capacitor. In such case the final position of the electrode unit is registered in the magnetic field of the corresponding eddy current probe.

A reverse switching of the capacitor plates of the given primary transducer restoring the initial position is preferably performed within the time interval between the final position of the controlled unit in the control zone of the given primary transducer and its initial position in the control zone of the next primary transducer.

The distance between the adjacent primary measuring transducers is determined by the linkage value of the electric fields of the last capacitor of the previous measuring transducer with the first capacitor of the subsequent measuring transducer. The calculation of this interaction for the distance between the plates specified in FIG. 1(*a*) (see Example 2) is given in Example 4. The results of the calculation show that with an one percent accuracy the distance between the lateral end face of the plates of the last capacitor of the previous measuring transducer and the opposite lateral end face of the plates of the first capacitor of the subsequent measuring transducer is of the value that 1.5 times exceeds the maximum distance between the capacitor plates found on the opposite edges of the shell.

The conveyor belt vibrations during its movement lead to a change of the gap between the outer surface of the unit and the inner surface of the shell. As the magnetic field intensity of the eddy current probe varies along the axis ρ (see FIG. 10), this will lead to a change in the registered value of the introduced active resistance of the eddy current probe that introduces an error. The calculation of this error for the most typical single-turn eddy current probe is given in Example 5. The calculation results are shown in TABLE 4 of Example 5.

As follows from TABLE 4 the value of the coefficient γ determining the relative change of the active resistance introduced into the single-turn probe during the shift of the electrode unit in the radial direction resulting from the shift (during vibrations) of the conveyor belt, increases non-linearly with the increase of d. At the maximum shift d=0.65 mm γ=1.234, that is the error reaches 23.4%. To correct for this error, strap capacitors are used that are arranged at both sides of the eddy current probe.

As noted above, after registering the initial position of the electrode unit the plates of the capacitors in the primary measuring transducer are changed-over. In such case the plates of the newly formed first capacitor are found on the one side of the controlled electrode unit (one at the left and the other at the right side of the of the eddy current probe) while the plates of the second capacitor are found on the other side of the electrode unit in the same manner.

When the conveyor belt with the electrode unit is shifted in the direction perpendicular to the movement (that is either down or up) the capacitance of one of the capacitors gets increased while that of the second capacitor gets correspondingly decreased depending on the shift direction of the unit. In such case the capacitor whose capacitance is increasing is selected as the operating capacitor.

A situation when the conveyor belt is lifted in the process of its shift is now considered. Then the operating capacitor is that one that is comprised of the two switched in series capacitors each of the capacitance $C_a$ (see Example 2). Hence, the capacitance of the operating capacitor in its initial state $C_{w0}=C_a/2$. The change of the capacitance $C_a$ during the shift d of the electrode unit is shown in TABLE 2 of Example 2. The obtained results are well described by the approximating dependence:

$$C_w(d)=C_{w0} \cdot (1+4d^2), \quad (1)$$

Where $C_{w0}$ is the operating capacitance at the zero shift of the electrode unit. The values C are expressed in pF, where d is the shift value expresses in mm. Hence, the shift value d can be determined by the value of the operating capacitance.

The error of the introduced impedance of the eddy current probe occurring following a shift of the moving conveyor belt perpendicularly to the movement direction is reflected by the value γ calculated in Example 5 and given for various shift values d in the third column of TABLE 4. This dependence is well approximated by the following formula:

$$\gamma=1+d^2/2 \quad (2)$$

Where d is measured in mm.

Thus, knowing the value d that is obtained through measuring the operating capacitance and substituting it in (2), the value of the correcting coefficient γ for the introduced active resistance measured by means of the eddy current probe is determined, and in case of the first eddy current probe—for the active and the reactive resistance values.

In the process of manufacturing a dry electrode unit the uniformity of locating the cathode and anode strips inside of the unit may not be maintained. In other words, the distance between the cathode and anode strips in different layers of the electrode unit coil can differ thus leading to a change in the sensitivity of the introduced active resistance of the eddy current probe to coat defects. This results in the eddy currents flowing along the contacting surfaces of the coats of the cathode and anode strips are directed in opposite directions and attenuate each other to a certain degree by the interaction of their magnetic fields. This effect is increased when the cathode and anode strips approach each other. In its turn, the attenuation of the eddy currents induced in the coats reduces the sensitivity to defects in the material of the coat.

A frequency reduction of the primary magnetic field provided by the eddy current probe will lead to the concentration of eddy currents in the cathode and anode metallic strips. In such case the influence of the coat defects plummets. At the same time the packing density of the metallic strips or actually the distance therebetween will influence the magnetic field intensity of the eddy currents in the direction to the primary field of the probe thus determining the value of its introduced reactive resistance. The experiments held by us showed that the value of the introduced reactive resistance of the eddy current probe operating at a relatively low frequency (40 MHz in our case) practically did not depend on the presence of defects in the coat and was determined by the packing density of the cathode and anode metallic strips in the electrode unit. The methodology and the results of the performed experiment are described in Example 6. According to FIG. 7, with the reduction of the distance between the cathode and anode strips the value of the introduced into the eddy current probe relative reactive resistance and relative introduced inductance $L_{ad}/L_0$ gets lower.

The corrected relative to the conveyor belt vibrations values of the introduced reactive resistance of the first eddy current probe for all the controlled units preceding the given unit are preferably averaged. In this way is determined for the given unit the reference value that corresponds to the statistically uniform distribution of the metallic strips inside of the unit.

The value of the introduced reactive resistance of the first eddy current probe for the given unit is stored and then used for correcting the sensitivity of the second and subsequent eddy current probes when they subsequently control this electrode unit.

The sensitivity is corrected by multiplying the introduced active resistance for the second and subsequent probes by the relation of the averaged value of the introduced reactive resistance of the first probe for all the electrode units preceding the given one, to the value of the introduced reactive resistance of the same first probe for the given unit.

A closed circuit of the eddy current of substantial intensity is formed either by the linkage of the outer layer of the foil on the electrode unit surface or by strapping the metallic cathode and anode strips inside of the unit. This is accompanied by a substantial increase of the dissipated energy of the primary field and by a respective increase of the introduced active resistance of the probe. Due to the high conductance of the metallic strips in the electrode unit a substantially higher relative increase is observed of the introduced active resistance at the frequency of 40 MHz than at the frequencies of 150–180 MHz (see Example 1, FIGS. 3–7).

Therefore the electrode units with closed metallic layers are detected by the value of the introduced active resistance of the first eddy current probe operating at a substantially lower frequency in comparison to the others.

The modulation characteristic of the introduced impedance of the eddy current probe is measured in the interval of the initial and final positions of the electrode unit.

The electrode units that have defects in the coats of the cathode and anode strips are determined according to the corrected values of the introduced active resistance of the high frequency eddy current probes when they exceed the specified threshold. The latter is established on the basis of studying the selected units and comparing the obtained results with the X-ray data. It is often advisable to use units with artificially formed defects to obtain data from faulty units.

The current averaging is performed of the corrected values of the introduced active resistance of each of the high frequency eddy current probes for all the faultless units preceding the given faulty unit.

The relations are determined of the corrected amplitude values of the modulation characteristics of the relative (to the own induction resistance) introduced active resistance of each high frequency eddy current probe for the faulty unit being controlled, to the average values of the introduced active resistance of the probes that were obtained for all faultless units preceding the given faulty unit.

The obtained relations are compared for each operating frequency of the high-frequency band, and the maximum relation is determined that characterizes the defectiveness degree of the coats on the cathode and anode metallic strips of a dry electrode unit. This procedure is described in Example 7 for the units the study results of which are given in Example 1.

EXAMPLES

It should be understood that the Examples described below are provided for illustrative purposes only and do not in any way define the scope of the invention.

Example 1

This Example shows the results of studying samples of dry electrode units of lithium-ion batteries. In all 12 units were studied (the units were numbered from 1 to 13 excluding number 3 that was disassembled).

To study the resistance to defects of the anode and cathode coats of the units they were subjected to compression in a press at various loads at the vendor site. The loads are given in Table 1.

The electrode unit samples No. 1, 11, 12, 13 were not subjected to loads.

TABLE 1

| | No. of unit | | | | | | | | | | | |
|---|---|---|---|---|---|---|---|---|---|---|---|---|
| | 1 | 2 | 4 | 5 | 6 | 7 | 8 | 9 | 10 | 11 | 12 | 13 |
| Load, kg | 0 | 250 | 750 | 1000 | 1250 | 1500 | 2000 | 5000 | 10000 | 0 | 0 | 0 |

By visual inspection it was found that samples No. 8 and 10 have a closed outer layer of foil, while in sample No. 10 this layer was partially destroyed and the contact area was less.

Five (5) eddy current probes were used for studying the samples of the electrode units. The first of them contained W=6 turns of copper wire with a diameter $d_0=1$ mm, densely wound. The operating frequency of this probe was $f_1=40$ MHz. The turns of the probe were wound on a core made of a dielectric whose section shape repeated the section shape of the electrode unit. The core wall thickness was 0.5 mm. Q-factor meters were used for the studies: Tesla BM-409G and HP 4342A.

The results of the studies are shown in FIGS. 3–7. On the ordinate the values of the introduced active resistance were plotted that are rated relative to the own inductive resistance of the probe, while on the abscissa is the number of an electrode unit.

Figure 3:
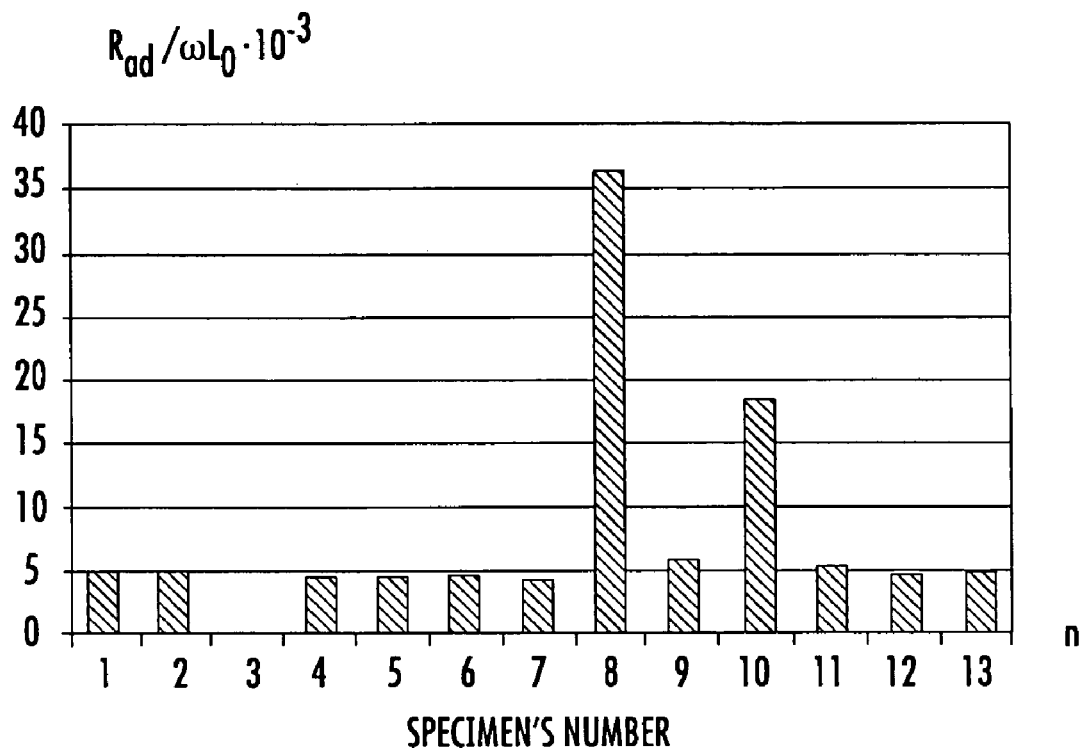
FIG. 3 provides values of the relative, introduced into the eddy current probe of the first measuring transducer, active resistance $R_{ad}/\omega L_0$ at 40 MHz frequency, and of the probing magnetic field for the studied dry electrode units (Jelly rolls). n is the unit number, as it is in FIGS. 4–7 as well.
Figure 4:
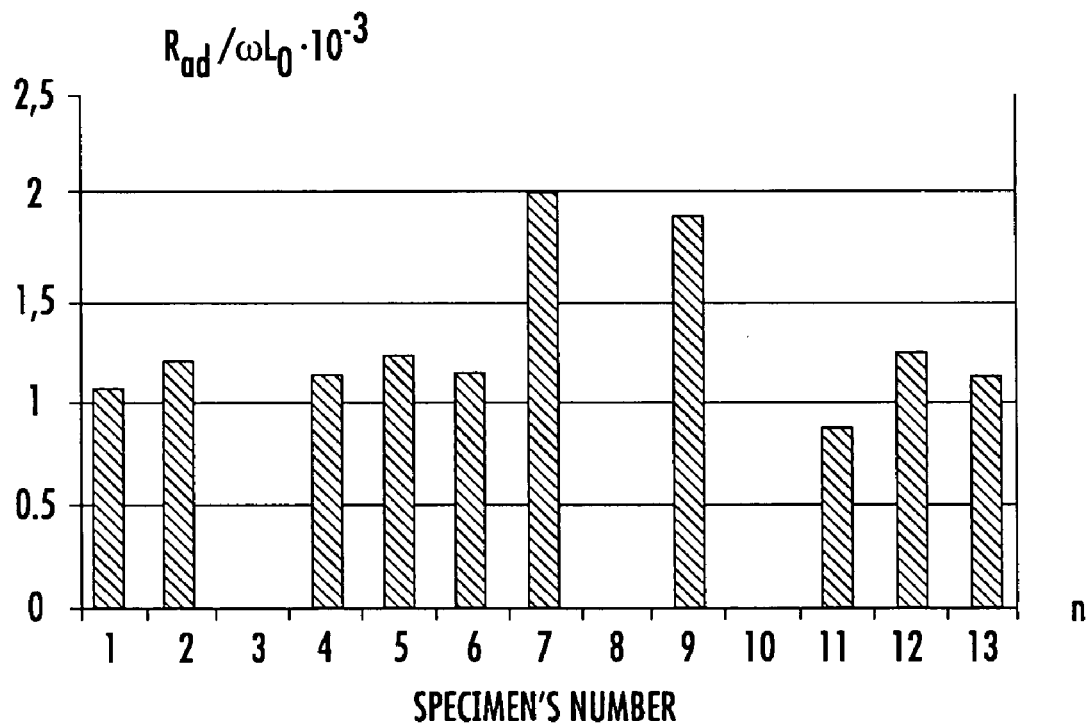
FIG. 4 provides values of the relative, introduced into the eddy current probe of the second measuring transducer, active resistance $R_{ad}/\omega L_0$ at 150 MHz frequency, and of the probing magnetic field for the studied dry electrode units (Jelly rolls).
Figure 5:
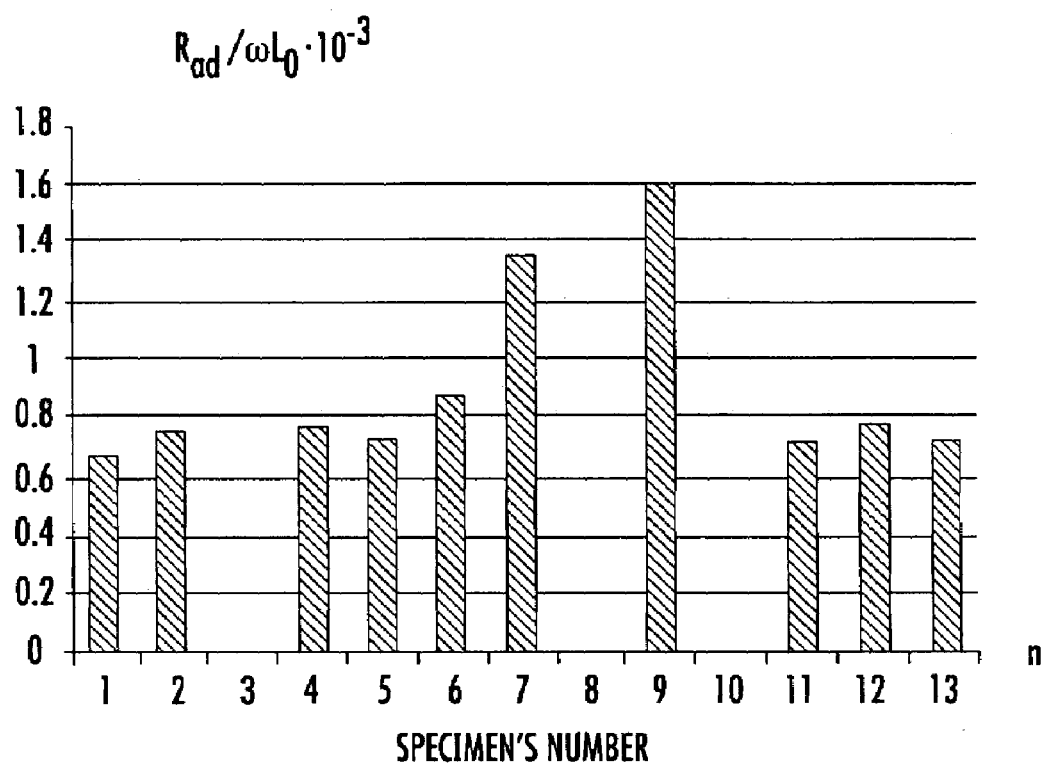
FIG. 5 provides values of the relative, introduced into the eddy current probe of the third measuring transducer, active resistance $R_{ad}/\omega L_0$ at 160 MHz frequency, and of the probing magnetic field for the studied dry electrode units (Jelly rolls).
Figure 6:
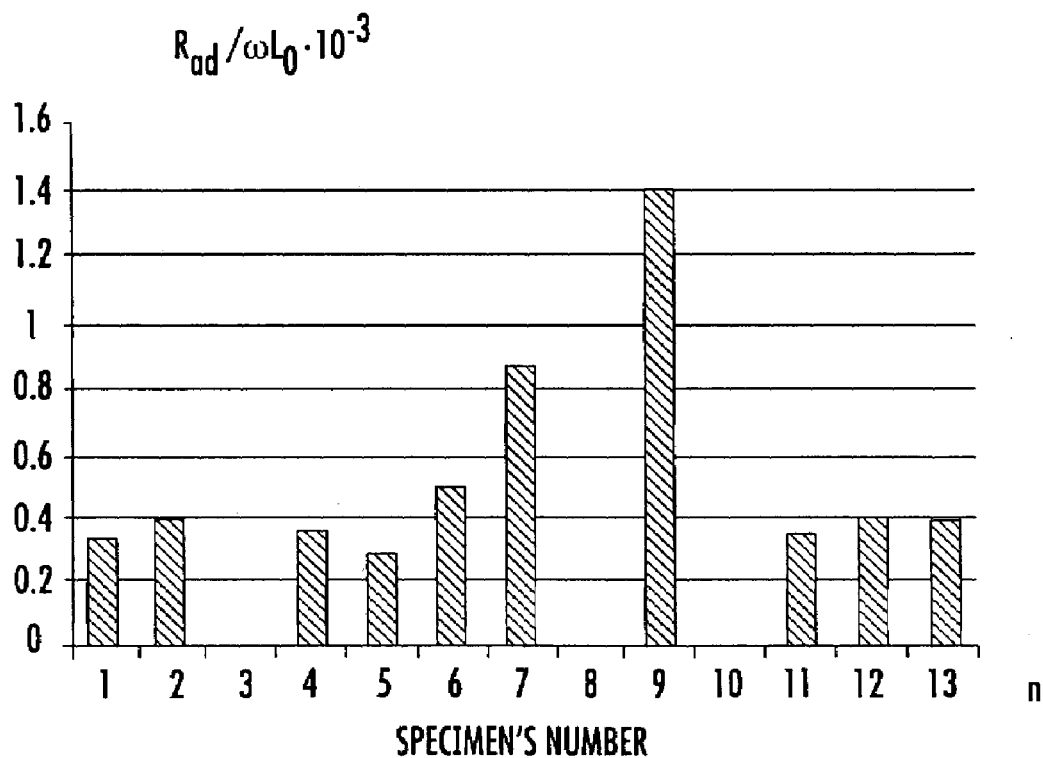
FIG. 6 provides values of the relative, introduced into the eddy current probe of the fourth measuring transducer, active resistance $R_{ad}/\omega L_0$ at 170 MHz frequency, and of the probing magnetic field for the studied dry electrode units (Jelly rolls).

The data given in FIG. 3 was obtained at the frequency of the probing magnetic field $f_1=40$ MHz. It is seen that among the group of the units are clearly distinguished units No. 8 and No. 10. In these units, as it was mentioned above, the outer foil layer is closed, while in the unit No. 8 the contact area is substantially larger than in unit No. 10.

Figure 7:
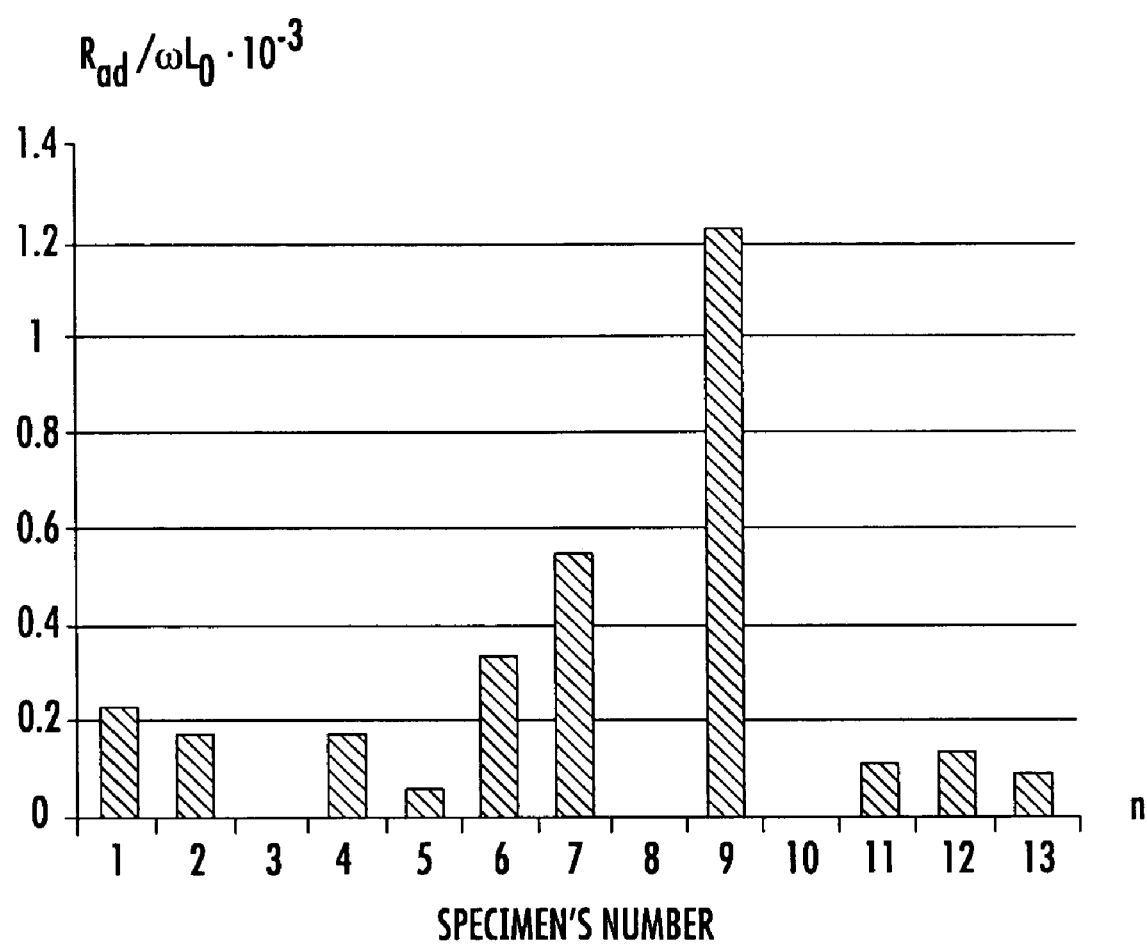
FIG. 7 provides values of the relative, introduced into the eddy current probe of the fifth measuring transducer, active resistance $R_{ad}/\omega L_0$ at 180 MHz frequency, and of the probing magnetic field for the studied dry electrode units (Jelly rolls).

In the next graphs are shown the results obtained for the samples of the units that were not distinguished at the frequency of 40 MHz. Single-turn probes were used with frequencies f2=150 MHz (FIG. 4), f3=160 MHz (FIG. 5), f4=170 MHz (FIG. 6), f5=180 MHz (FIG. 7).

The process of forcing the currents to the surface with the increase of frequency will be more intensive in the layers of higher conductance, that is in aluminum and copper. This process is clearly seen when studying the relation that determines the penetration depth of the eddy currents in the conducting medium (in this case as the penetration depth δ is understood such a depth at which the surface density of the eddy current is reduced by e times):

$$\delta = (\pi f \sigma \mu_0)^{-1/2}, \qquad (3)$$

where f is the frequency of the primary field of the eddy current transducer, σ is the specific electrical conductance of the conducting medium, $\mu_0$ is the magnetic permeability of the vacuum. It follows from formula (3) that with increasing frequency the penetration depth of eddy currents is reduced, in other words, their more substantial, in percentage, fraction will flow on the electrode coats of the copper and aluminum electrode strips. In such case a disturbance of the continuity of the layers in the electrode coats will lead, due to a change in the eddy current trajectories, to an increase in the rate of the active losses in the primary field of the probe, and a corresponding increase of the active resistance introduced into the probe.

From the comparison of the graphs shown in FIGS. 4–7 it is clear that for all the frequencies higher values of Rad/ωL0 feature samples No. 7 and 9. At the frequencies of 170 and 180 MHz (FIGS. 6 and 7 respectively) they are also added by the sample No. 6. According to the results of eddy current control these units should be considered defective, while the defectiveness degree of the coat in the unit No. 9 is maximal.

To verify the obtained results all the electrode units were subjected to X-ray inspection simultaneously with the sensitivity references. In such case the achieved sensitivity of X-ray examination allows to reveal defects at depths beginning from 100 μm.

Figure 8:
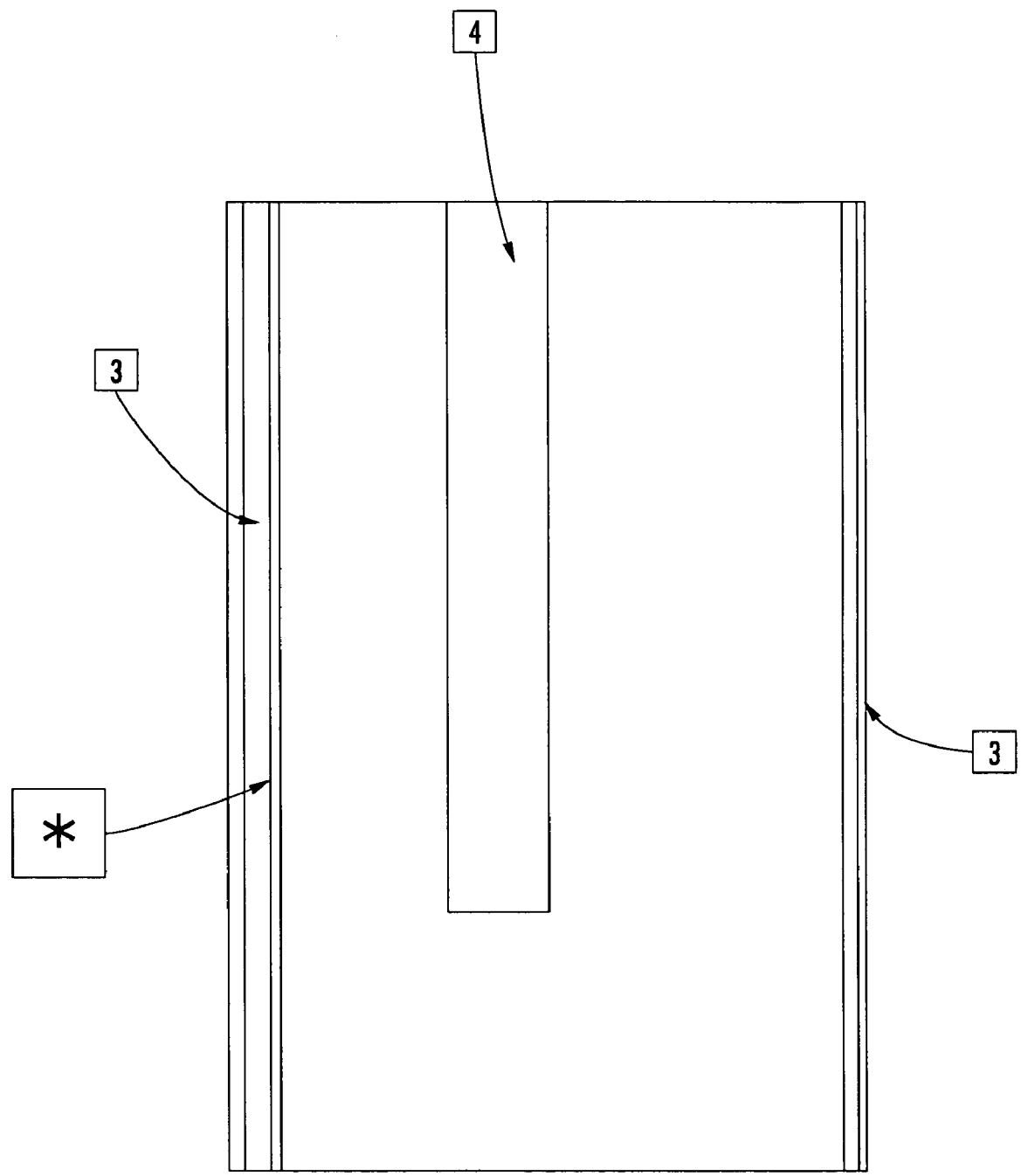
FIG. 8 is a scanned X-ray photograph of sample No. 13 that was not subjected to load; reference 3 indicates coat cracking on rounding-offs, reference 4 indicates the plate of a copper current conductor.
Figure 9:
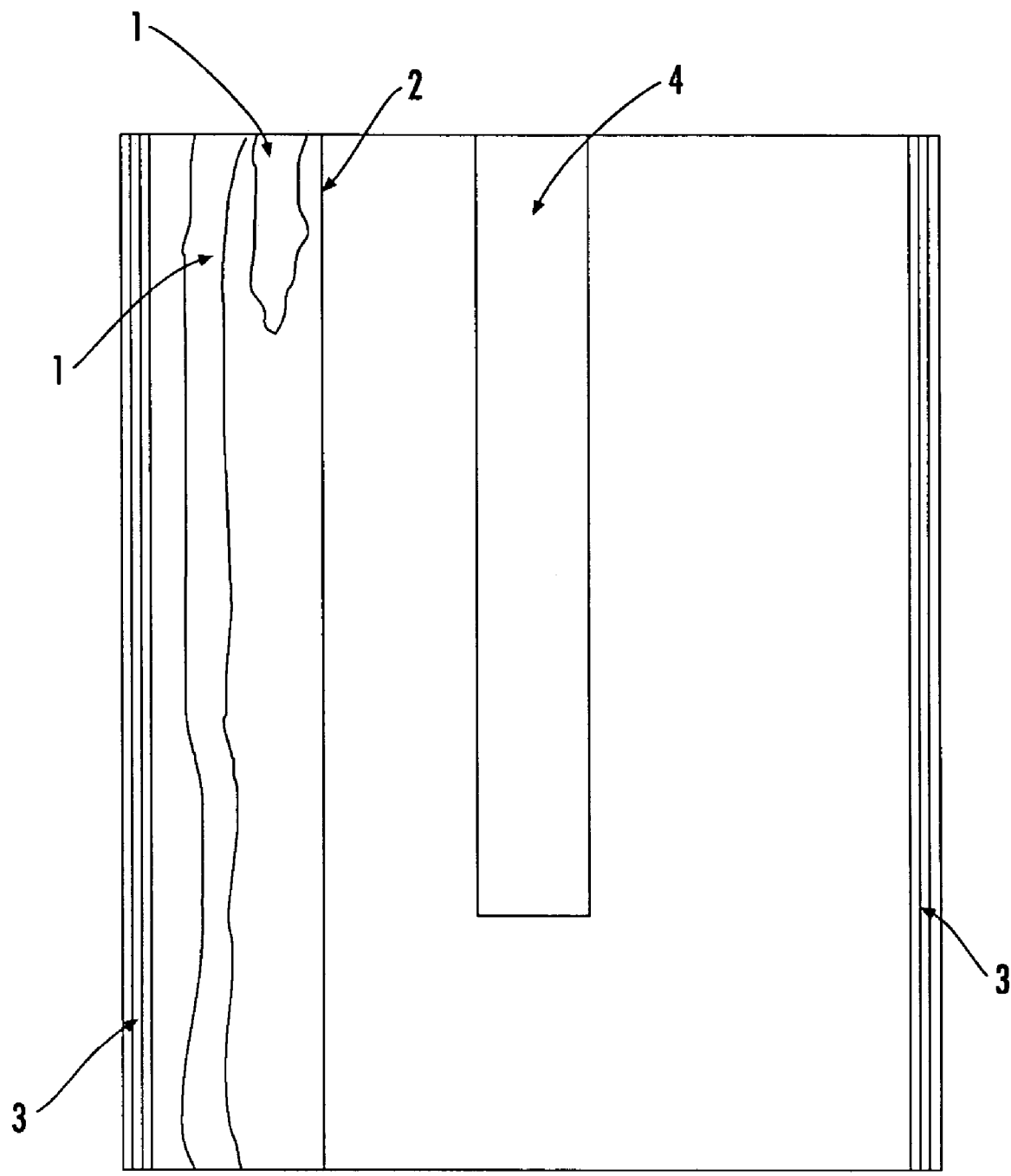
FIG. 9 is a scanned X-ray photograph of sample No. 9: reference 1 indicates coat chipping-off, reference 1' indicates coat spalling, reference 2 indicates deformation of the aluminum plate current intake under the applied load, reference 3 indicates coat cracking on rounding-offs, and reference 4 indicates a plate of a copper current conductor.

FIG. 8 shows a scanned photo from an X-ray image of sample No. 13 that was not subjected to any load. The scanned image picture in FIG. 8 shows that no significant defects were found, besides the minor coat cracking on the round-offs of the electrode strips. The results of the eddy current test performed on this control did not reveal any defect.

Around the same time, an X-ray photo of sample No. 9 was taken. Sample No. 9 was identified as the sample with the maximum coat continuity defects, respectively, based on eddy-current data obtained. A large chip-off is seen in the coat that propagates along the unit length to a considerable depth; besides, in the left part of the picture a light strip is recorded over the whole length of the unit. Usually it is considered as an indicator of the coat spalling. Unit No. 9 is considered to be the most defective judging by the results of eddy current control. The presence of a chip-off that is approximately twice less in its length than in unit No. 9 was also recorded in unit No. 7.

Example 2

This Example contains an approximate calculation of the initial capacitance of the capacitor whose plates are placed on a dielectric shell surrounding the conveyor belt. The shape and the dimensions of the shell correspond to the electrode units the results of whose studies are discussed in Example 1. The 5 mm wide plates are placed in the slot of the shell so that the wall thickness of the shell in the place where the plate is arranged equals 5 mm.

Taking into regard the shape of the shell that in its perpendicular section is similar to the shape of a cylindrical jelly roll electrode unit, it can be accepted in the first approximation that the capacitor plates are plane while the capacitor is plane-parallel (see FIG. 1(a)).

Such a capacitor can be replaced with a chain of five connected in series capacitors (C1, C2, C3, C4, C5). Here C1=C5 is the capacitance of the dielectric wall of the shell in the place where the plates are located; C2 is the capacitance of the larger air gap between the inner wall of the shell and the upper surface of the conveyor belt; C3 is the capacitance of the conveyor belt of surface area S that is equal to the surface area of electrodes 1 (see FIG. 10) of the capacitor; C4 is the capacitance of the smaller air gap between the lower surface of the conveyor belt and the inner wall of the shell.

Hence $$\frac{1}{C_e} = \frac{1}{S}\left(\frac{2T_1}{\varepsilon_1} + \frac{T_2}{\varepsilon_0} + \frac{T_3}{\varepsilon_3} + \frac{T_4}{\varepsilon_0}\right) \quad (4)$$

where $T_i$ and $\varepsilon_i$ are the thickness and the dielectric permeability values of the corresponding layers.

It is now assumed that the dielectric permeability of the casing material equals $\varepsilon_1=6$; such dielectric permeability has, for example glass-cloth-base laminate. The dielectric permeability of the conveyor belt shall be assumed to be $\varepsilon_3=4$. Assuming the width of the capacitor plate to be 5 mm, and its length 40 mm, $S=0.2\cdot 10^{-3}$ m is obtained. In such case the capacitance value of the capacitor $C_e=0.16$ pF. This is the capacitance of the capacitor without a sample (initial capacitance).

Figure 11:
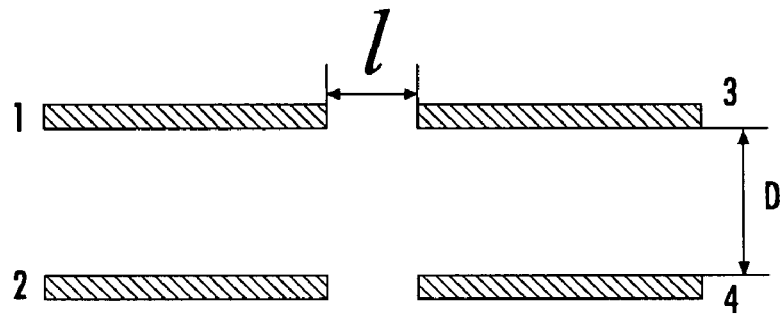
FIG. 11 is a figure helpful in calculating the minimum allowable distance between the adjacent measuring transducers: references 1 and 2 are plates of the second capacitor of the preceding measuring transducer, references 3 and 4 are plates of the first capacitor of the subsequent measuring transducer.

Again with reference to FIG. 1(b), the situation when an electrode unit 4 (CONFIRM) moving on the conveyor belt 3 in dielectric shell 2 assumes a position between the plates of the capacitor 1 is shown in FIG. 11. On the surface of the unit is the aluminum foil that screens the potential electric field of the capacitor plates. The capacitance of the capacitor is determined in such case when our capacitor having the capacitance $C_e$ will consist of two series connected capacitors $C_a$ and $C_b$ whose inner plates will be connected on the foil of the outer shell of the electrode unit 4. Hence $$C_t = \frac{C_a \cdot C_b}{C_a + C_b}. \quad (5)$$

The capacitance of the capacitor $C_a$ will be determined by the two series connected capacities: $C_1$—the capacitance of the dielectric wall of the shell 2 and $C_2$—the capacitance of the air gap between the inner surface of the dielectric shell 2 and the outer metallic surface of the electrode unit. Therefore $$\frac{1}{C_a} = \frac{1}{C_1} + \frac{1}{C_2}. \quad (6)$$

The capacitance of the capacitor $C_b$ is determined by the three series connected capacities:

$$\frac{1}{C_b} = \frac{1}{C_3} + \frac{1}{C_4} + \frac{1}{C_5}, \quad (7)$$

where $C_3$ is the capacitance of the electrode strip found in the field of the plates, $C_4$ is the capacitance of the air gap between the lower surface of the conveyor belt and the inner surface of the dielectric shell, $C_5=C_1$ is the capacitance of the dielectric wall of the shell.

By calculating value $C_1$ in accordance with the given expressions (5)–(7) and the geometrical dimensions shown in FIGS. 1(a) and (b), $C_1=0.91$ pF is obtained.

How the capacitance $C_1$ changes with the shift d of the electrode unit in the direction perpendicular to the capacitor plates is now described. Taking into account the shift value d (mm) and the actual dimensions of the system: capacitor plates—shell—conveyor belt—electrode unit that are given in FIGS. 1(a0 and (b), the expressions for calculating $C_a$ and $C_b$ will have the following form:

$$\frac{1}{C_a} = \frac{1}{S\varepsilon_0}\left[\frac{T_1}{\varepsilon_1} + (\Delta T_1 - d)\right], \quad (8)$$

$$\frac{1}{C_b} = \frac{1}{S\varepsilon_0}\left[\frac{T_1}{\varepsilon_1} + (\Delta T_2 + d) + \frac{T_3}{\varepsilon_3}\right], \quad (9)$$

where: $S=0.2\cdot 10^{-3}$ m—surface area of capacitor plate; $\varepsilon_0=8.85\cdot 10^{-12}$ F/m—dielectric permeability of vacuum; $T_1$ and $\varepsilon_1$—the thickness and dielectric permeability of the wall in the shell ($T_1=0.5$ mm и $\varepsilon_1=6$); $T_3$ and $\varepsilon_3$—the thickness and dielectric permeability of the conveyor belt ($T_3=0.3$ mm and $\varepsilon_3=4$); $\Delta T_1$ and $\Delta T_2$—corresponding gaps between the upper wall of the shell and the surface of the electrode unit, and the lower wall of the shell and the lower surface of the conveyor belt in the initial symmetric position of the electrode unit ($\Delta T_1=1$ mm and $\Delta T_2=0.7$ mm); where d is the unit shift value in mm.

The calculated capacitance values $C_a$, $C_b$ and $C_1$ are given in TABLE 2. As TABLE 2 shows, the value of the capacitance $C_1$ being measured (loaded capacitor) practically does not change with the shift of the electrode unit in the direction perpendicular to the capacitor plates, that is perpendicularly to the uniform movement direction of the conveyor belt.

TABLE 2

| d, mm | $C_a$, pF | $C_b$, pF | $C_l$, pF |
|---|---|---|---|
| 0 | 1.63 | 2.06 | 0.910 |
| 0.1 | 1.80 | 1.847 | 0.911 |
| 0.25 | 2.125 | 1.597 | 0.912 |
| 0.4 | 2.592 | 1.407 | 0.912 |
| 0.5 | 3.036 | 1.303 | 0.912 |
| 0.65 | 4.087 | 1.173 | 0.911 |

Example 3

This example contains the calculation of the intensity components of the magnetic field of a turn under current for determining the distance between the turn of the eddy current probe and the capacitor plate.

Figure 10:
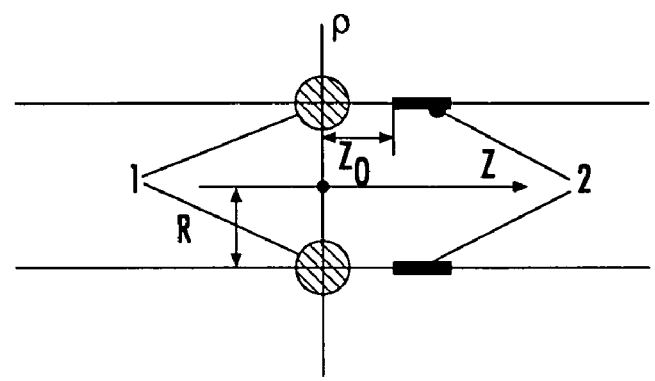
FIG. 10 shows relevant distances for calculating the distance between the capacitor plates and turn of the eddy current probe: 1 indicates a turn of the probe, 2 indicates capacitor plates, ρ and z are coordinates of the cylindrical coordinate system.

The mutual position of the turn and the plates is schematically shown in FIG. 10. The expressions of the intensity components of the magnetic field of circular current has the following form:

$$H_\alpha = 0 \quad (10)$$

$$H_\rho = \frac{I}{2\pi\rho} \cdot \frac{z}{[(R+\rho)^2 + z^2]^{1/2}} \left[ -K + \frac{R^2 + \rho^2 + z^2}{(R-\rho)^2 + z^2} N \right];$$

$$H_z = \frac{I}{2\pi} \cdot \frac{1}{[(R+\rho)^2 + z^2]^{1/2}} \left[ K + \frac{R^2 - \rho^2 - z^2}{(R-\rho)^2 + z^2} N \right].$$

Here R is the turn radius, K and N are the full elliptic integrals of the first and second type. The approximate expressions (in series form) for these integrals are given below.

$$\frac{2}{\pi}K = 1 + 2\frac{k^2}{8} + 9\left(\frac{k^2}{8}\right)^2 + 50\left(\frac{k^2}{8}\right)^3 + \frac{1225}{4}\left(\frac{k^2}{8}\right)^4 + \ldots, \quad (11)$$

$$\frac{2}{\pi}N = 1 - 2\frac{k^2}{8} - 3\left(\frac{k^2}{8}\right)^2 - 10\left(\frac{k^2}{8}\right)^3 - \frac{175}{4}\left(\frac{k^2}{8}\right)^4 + \ldots, \quad (12)$$

where $k^2 = \frac{4\rho R}{(R+\rho)^2 + z^2}$.

The corresponding intensity values $H_\rho$ and $H_z$ on the line $\rho = R$ (see FIG. 10) are now calculated. On this line the intensity components can be presented in the form:

$$H_\rho = \frac{I}{4R} \cdot \frac{z}{[4R^2 + z^2]^{1/2}} \left[ -\frac{2}{\pi}K + \frac{2R^2 + z^2}{z^2} \cdot \frac{2}{\pi}N \right]; \quad (13)$$

$$H_z = \frac{I}{4} \cdot \frac{1}{[4R^2 + z^2]^{1/2}} \left[ \frac{2}{\pi}K - \frac{2}{\pi}N \right].$$

The calculation results are given in TABLE 3.

TABLE 3

| z/R | s | t | $H_z/H_\rho$ |
|---|---|---|---|
| 0.01 | 1.0 | 1.0 | 0.0076 |
| 0.1 | 0.1158 | 1.0 | 0.065 |
| 0.2 | 0.0558 | 1.0 | 0.13 |
| 0.4 | 0.0239 | 0.96 | 0.32 |
| 1.0 | 0.0071 | 0.61 | 0.66 |
| 2.0 | 0.0014 | 0.25 | 1.32 |

Here
$s = H_\rho(\rho = R, z)/H_\rho(\rho = R, z = 0.01R)$;
$t = H_z(\rho = R, z)/H_z(\rho = R, z = 0.01R)$.

The calculation results given in Table 3 show that already at the distance z=0.2R the tangential component of the field intensity $H_\rho$ comprises 5.58% of the intensity $H_\rho$ at the distance z=0.01R from the turn section; at the distance z=0.4R the value $H_\rho$ equals 2.39%.

Value $H_z$ decreases much slower with the increase of z/R (see the column for t of the Table). However, as follows from the fourth column, its intensity at z=0.2R comprises 13% of $H_\rho$, and at the distance z=0.4R—32%.

Thus the distance $z_0$ (see FIG. 10) can be selected to be equal to $z_0 = 0.4R$, with an accuracy that is satisfactory for practical uses.

Example 4

This example contains the calculation of the capacitance relation between the two capacitors (see FIG. 11) whose dimensions are determined in Example 2 (see FIG. 1(*a*)). The relation is calculated using the following formula:

$$\delta = \frac{\Delta C}{C} = e^{-\frac{\pi \cdot l}{D}} \quad (14)$$

where $\Delta C$ is the change of the capacitance C of each of the capacitors due to the mutual linkage of the electric fields, l is the gap between the lateral end faces of the plates in these capacitors, D is the distance between the plates of the capacitors.

At l=D δ=4.3%; at l=1.5D δ=0.9%; at l=2D δ=0.18%. Formula (14) is approximate, but it allows evaluating the minimum distance l between the end faces of the capacitors. In the present case, at D=12 mm (see FIG. 1(*a*)) this distance should be assumed to be equal to 18 mm. In this case δ=0.9% and in practice the linkage between the capacitors of the adjacent measuring transducers can be neglected.

Example 5

This example shows calculation of the error related to a vertical shift of the electrode unit on the conveyor belt in the field of the current turn (the conveyor belt is assumed to move at a constant speed in the horizontal direction).

The electrode unit surface is coated with a metallic foil that usually has a cutting of about 1 mm width along its generatrix. Under the action of the primary field on the outer surface of the foil a turn of the eddy current is induced whose trajectory shape is similar to the shape of the turn in the eddy current probe.

As it is known from the theory of the magnetic field, the interaction intensity of the fields of the two such turns, and, correspondingly, the impedance introduced into the primary turn (field source) are determined by the squared value of the mutual inductance of the turns.

In such case for round turns of radius $R_1$ (the turn of the eddy current probe) and $R_2$ (the turn of the eddy current), whose centers are shifted by the value d, the expression for mutual inductance has the following form [4]:

$$M = \pi\mu_0 \frac{R_2^2}{R_1} \sum_{n=0}^{\infty} (-1)^n \frac{(2n+1)!}{2^{2n+1}(n!)^2} \left(\frac{d}{R_1}\right)^{2n} \cdot F\left(n+\frac{1}{2}, n+\frac{3}{2}, 2, \frac{R_2^2}{R_1^2}\right) \cdot P_{2n}(\cos\Theta), \quad (15)$$

where F is the hypergeometric progression, $P_{2n}$ is the Legandre's polynomial, $\Theta=\pi/2$.

According to FIGS. 1(a) and 1(b), $R_1=6$ mm and $R_2=4.5$ mm. The shift value d changes within the range of d=0–0.65 mm, as according to FIG. 1(a) the gap between the lower surface of the conveyor belt and the inner surface of the shell wall, equals 0.7 mm, thus it is assumed that the vibration amplitude of the conveyor belt in the direction perpendicular to the movement direction is limited to 0.7 mm.

Table 4 contains the squared values of the mutual inductance $M^2$ calculated by formula. In the third column of the table are the rated values of the squared mutual inductance. The rating is performed with reference to value $M^2$ at zero shift d=0.

TABLE 4

| d, mm | $M^2 \cdot 10^{-14}$ Hn$^2$ | $\gamma = M^2(d)/M^2(d=0)$ |
| --- | --- | --- |
| 0 | 0.00545 | 1.000 |
| 0.1 | 0.00546 | 1.002 |
| 0.25 | 0.00554 | 1.016 |
| 0.4 | 0.0057 | 1.046 |
| 0.5 | 0.00603 | 1.106 |
| 0.65 | 0.00673 | 1.234 |

As follows from Table 4, at the maximum deviation d=0.65 mm value $M^2$ increases by 23.4% relative to the symmetrical position of the electrode unit, that is without any shift in the vertical direction (d=0).

Example 6

This example describes the studies of the influence of the packing density in the layers of dry electrode units on the value of the introduced reactive resistance of the first eddy current probe.

The units described in Example 1 were used in the studies. These electrode units were preliminary subjected to compression under loads specified in Table 1, the thickness of the electrode units in these conditions was changed, and the packing density of the layers differed correspondingly.

Figure 12:
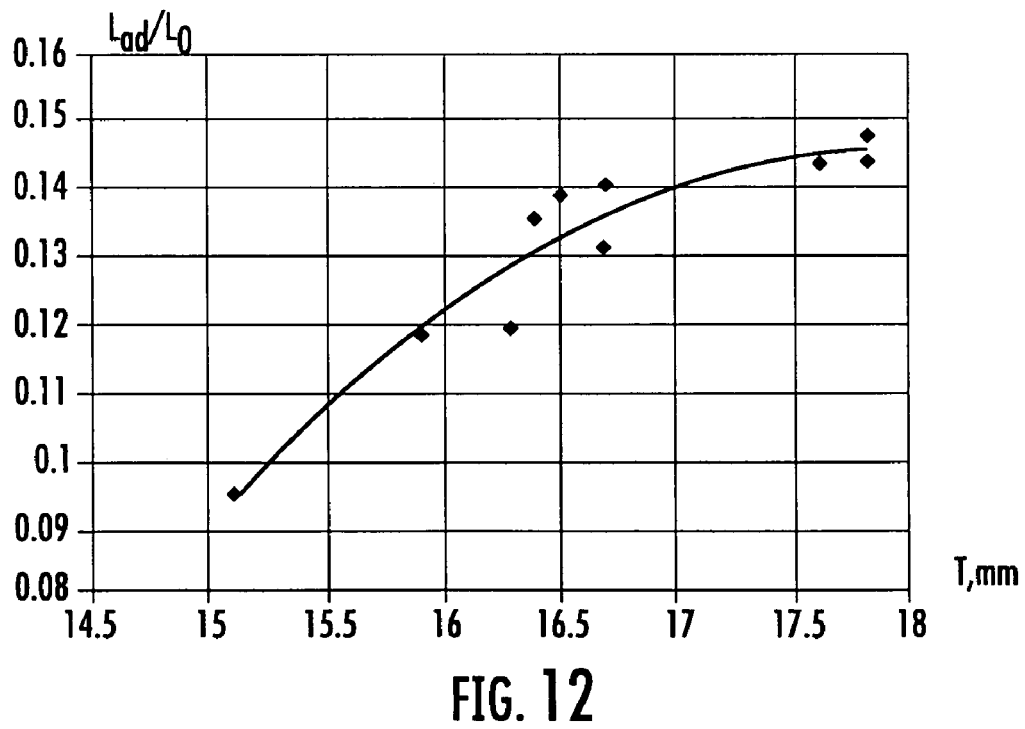
FIG. 12 provides values of the relative inductance introduced into the eddy current probe of the first measuring transducer inductance $L_{ad}/L_0$ at 40 MHz frequency and of the probing magnetic field for the studied dry electrode units (Jelly rolls). Here n is the unit number.

The measurements were performed at the frequency of 40 MHz using a feed-through eddy current probe containing W=6 turns of copper wire of diameter $d_0=1$ mm. Q-factor meter type HP4342A was used in the measurements. The shape and dimensions of the radial section of the winding in each eddy current probe corresponded to the shape and dimensions of the section of each unit being studied. The value of the introduced reactive resistance of the eddy current probe was registered as rated to the value of its own inductive resistance. The obtained results are shown in FIG. 12. It is seen that with the reduction in the thickness of the unit, that is with the increase of the packing density of the layers (or reduction of the distance between the layers) the value of the relative introduced reactive resistance or, which is the same, of the relative introduced inductance $L_{ad}/L_0$ reduces monotonously.

Example 7

Described in this Example is the methodology of processing the eddy current control results experimentally obtained in Example 1. For the eddy current probe with control frequency 150 MHz (data shown in FIG. 4), assuming as the threshold level $\Delta=1.5 \cdot 10^{-3}$, units No. 7 and No. 9 are identified as defective units. In this case the average value $R_{ad}/\omega L_0$ for all faultless units will approximately equal $1.1 \cdot 10^{-3}$. Then the relation of the introduced active resistance $R_{ad}/\omega L_0$ for the faulty unit No. 7 to the average value for all faultless units will be $\alpha_7=1.82$, for the faulty unit No. 9—$\alpha_9=1.68$.

For the eddy current probe with control frequency 160 MHz (data shown in FIG. 5), assuming as the threshold level $\Delta=0.8 \cdot 10^{-3}$ units No. 7 and No. 9, as well as unit No. 6 were identified as defective units. In this case the average value $R_{ad}/\omega L_0$ for all faultless units will approximately equal $0.73 \cdot 10^{-3}$. Then the relation of the introduced active resistance $R_{ad}/\omega L_0$ for the faulty unit No. 6 to the average value for all faultless units will be $\alpha_6=1.16$, for the faulty unit No. 7—$\alpha_7=1.86$, for the faulty unit No. 9—$\alpha_9=2.21$.

For the eddy current probe with control frequency 170 MHz (data shown in FIG. 6), assuming as the threshold level $\Delta=0.45 \cdot 10^{-3}$, units No. 6, No. 7 and No. 9 were identified as defective units. In this case the average value $R_{ad}/\omega L_0$ for all faultless units will approximately equal $0.37 \cdot 10^{-3}$. Then the relation of the introduced active resistance $R_{ad}/\omega L_0$ for the faulty unit No. 6 to the average value for all faultless units will be $\alpha_6=1.35$, for the faulty unit No. 7—$\alpha_7=2.35$, for the faulty unit No. 9—$\alpha_9=3.76$.

For the eddy current probe with control frequency 180 MHz (data shown in FIG. 7), assuming as the threshold level $\Delta=0.25 \cdot 10^{-3}$, No. 6, No. 7 and No. 9 were identified as defective units. In this case the average value $R_{ad}/\omega L_0$ for all faultless units will approximately equal $0.22 \cdot 10^{-3}$. Then the relation of the introduced active resistance $R_{ad}/\omega L_0$ for the faulty unit No. 6 to the average value for all faultless units will be $\alpha_6=1.5$, for the faulty unit No. 7—$\alpha_7=2.55$, for the faulty unit No. 9—$\alpha_9=5.55$.

The obtained values $\alpha_i$ for all faulty units and control frequencies are listed in Table 5.

TABLE 5

| Control frequency, f, MHz | Nos. of faulty units | | |
| --- | --- | --- | --- |
| | No. 6 | No. 7 | No. 9 |
| 150 | — | 1.82 | 1.68 |
| 160 | 1.16 | 1.86 | 2.21 |
| 170 | 1.35 | 2.35 | 3.76 |
| 180 | 1.5 | 2.55 | 5.55 |

When comparing the relation values $\alpha_i$, listed in Table 5, the maximum relations for each faulty unit should be specified. All of them were obtained at the frequency of 180 MHz. As the maximum value of the relation $\alpha_{max}$ corresponds to the defectiveness degree of the electrode coat of the unit, the unit No. 6 should get the index $\alpha_{6max}=1.5$, unit No. 7—index $\alpha_{7max}=2.55$, unit No. 9—index $\alpha_{9max}=5.55$. These index values characterize the faulty units during their comparative evaluation and sorting (grading into separate groups).

This invention can be embodied in other forms without departing from the spirit or essential attributes thereof and, accordingly, reference should be had to the following claims rather than the foregoing specification as indicating the scope of the invention.

We claim:

1. A method of non-destructive non-contact quality inspection of dry electrode units of energy storage, including the steps of:
   providing an eddy current-based inspection system comprising a conveyor belt, and a hollow dielectric shell, an outer surface of said shell having a plurality of measuring transducers thereon, each of said transducers including a feed-through eddy current probe and at least two strap capacitors spatially linked therewith;
   placing an electrode unit to be inspected on said conveyor belt, wherein said electrode unit enters and moves through said dielectric shell;
   exciting said electrode unit using a magnetic field from said eddy current probe as it passes by each of said plurality of transducers while in said shell, wherein eddy currents at a plurality of frequencies are induced;
   measuring modulation characteristics of impedance at said plurality of frequencies using said eddy current probes, and
   determining whether said electrode unit is defective based on said modulation characteristics of said impedance.

2. The method of claim 1, wherein a generatrix of said shell is substantially parallel to a direction of movement of said conveyor belt, and a perpendicular section of said shell is similar in shape to a cross-sectional shape of said electrode unit.

3. The method of claim 1, further comprising the steps of:
   registering an initial and final position of said electrode unit in a magnetic field emanated from of each of said eddy current probes using said strap capacitors linked therewith, and
   correcting error in the introduced impedance of each of said eddy current probes that appears as a result of shifting of movement of said conveyor belt with said electrode unit in a direction that is perpendicular to a direction of said movement using signals obtained from said strap capacitors to provide corrected modulation characteristics of said impedance.

4. The method of claim 1, wherein said strap capacitors for each of said transducers are arranged on both sides of said eddy current probe at a substantially equal distance therefrom, and said plates of said strap capacitors are disposed on opposite sides of a surface of said shell opposite to one another.

5. The method of claim 1, wherein said plurality of eddy current probes operate at plurality of different frequencies.

6. The method of claim 5, wherein a first of said eddy current probes to measure said electrode unit operates at a lowest of said plurality of different frequencies, wherein said plurality of eddy current probes other than said first eddy current probe high frequency probes.

7. A system for non-destructive non-contact quality inspection of dry electrode units of storage batteries, comprising:
   an eddy current-based inspection system comprising a conveyor belt, and a hollow dielectric shell, an outer surface of said shell having a plurality of measuring transducers disposed thereon, each of said transducers including a feed-through eddy current probe and at least two strap capacitors spatially linked therewith.

8. The system of claim 7, wherein a generatrix of said shell is substantially parallel to a direction of movement of said conveyor belt, and a perpendicular section of said shell is similar in shape to a cross-sectional shape of said electrode unit.

9. The system of claim 7, wherein said strap capacitors for each of said transducers are arranged on both sides of said eddy current probe at a substantially equal distance therefrom, and said plates of said strap capacitors are disposed on opposite sides of a surface of said shell opposite to one another.

10. The system of claim 7, wherein a measuring transducer of a first of said eddy current probes to measure said electrode unit provides at least 5 times higher number of turns as compared to measuring transducers of other of said eddy current probes.

11. The system of claim 7, wherein a width of said conveyor belt does not exceed a width of said electrode unit.

12. The system of claim 11, wherein said conveyor belt is formed from a dielectric material with a dielectric loss tangent not exceeding $3 \times 10^{-3}$ within the metric wave band.

13. The system of claim 12, wherein said dielectric shell is formed from a dielectric material which provides a loss tangent not exceeding $10^{-3}$ within the metric wave band, with a wall thickness of said shell not exceeding 5 mm.

* * * * *